_(12)_ United States Patent
Tajima et al.

(10) Patent No.: US 7,731,944 B2
(45) Date of Patent: Jun. 8, 2010

(54) HAIR COSMETIC COMPOSITIONS

(75) Inventors: Sachiko Tajima, Tokyo (JP); Fumio Shibue, Tokyo (JP); Kenichi Kaneko, Tokyo (JP)

(73) Assignee: KAO Corporation, Tokyo (JP)

( * ) Notice: Subject to any disclaimer, the term of this patent is extended or adjusted under 35 U.S.C. 154(b) by 1398 days.

(21) Appl. No.: 11/084,032

(22) Filed: Mar. 21, 2005

(65) Prior Publication Data

US 2005/0160538 A1 Jul. 28, 2005

Related U.S. Application Data

(60) Division of application No. 10/404,083, filed on Apr. 2, 2003, now abandoned, which is a continuation-in-part of application No. 09/956,888, filed on Sep. 21, 2001, now abandoned.

(30) Foreign Application Priority Data

Sep. 21, 2000 (JP) ............................. 2000-286644

(51) Int. Cl.
*A61K 8/00* (2006.01)
*A61Q 5/08* (2006.01)
*A61Q 5/10* (2006.01)

(52) U.S. Cl. ...................... 424/70.1; 424/401; 424/62; 8/406

(58) Field of Classification Search ...................... None
See application file for complete search history.

(56) References Cited

U.S. PATENT DOCUMENTS

| 2,283,350 | A | | 5/1942 | Baum |
| 5,190,747 | A | | 3/1993 | Sekiguchi et al. |
| 5,938,792 | A | | 8/1999 | Lang et al. |
| 6,036,730 | A | | 3/2000 | Yoshida et al. |
| 6,342,079 | B1 | * | 1/2002 | Pan et al. ....................... 8/410 |

FOREIGN PATENT DOCUMENTS

| EP | 0 997 452 | | 5/2000 |
| GB | 2033939 | | 5/1980 |
| JP | 55-85512 | | 6/1980 |
| JP | 5-310543 | | 11/1993 |
| JP | 405310543 | A | 11/1993 |
| JP | 05-310543 | | 3/1997 |
| JP | 9-103473 | | 4/1997 |
| JP | 10-36228 | | 2/1998 |
| JP | 10-45553 | | 2/1998 |
| JP | 10-219272 | | 8/1998 |
| JP | 10-231234 | | 9/1998 |
| JP | 11-139923 | | 5/1999 |
| JP | 2000-143571 | | 5/2000 |
| JP | 2001-131037 | | 5/2001 |
| JP | 2001-151644 | | 6/2001 |
| JP | 2001-181164 | | 7/2001 |
| JP | 2000-286644 | | 4/2002 |
| KR | 10-1998-0042947 | | 5/2000 |

OTHER PUBLICATIONS

Database Reg, RN 127-51-5, (entered Nov. 16, 1984) STN.
Database Reg, RN 7388-22-9, (entered Nov. 16, 1984) STN.
Quarterly Perfumery and Flavoring (No. 204 Japan Perfumery and Flavoring Association, Dec. 30, 1999).
Sangyo Tosho Kabushiki Kaisha (Fundamental Knowledge of Fragrances and Perfumery).
Quarterly Perfumery and Flavoring (No. 149 Japan Perfumery and Flavoring Association, Mar. 1986).
JP 05-310543 Computer Translation.
Fragrance Journal, Jun. 1993, published by Fragrance Journal Co., Ltd., on Jun. 15, 1993, pp. 78-81, 111 (w/English abstract).
"Synthesized Fragrances—Chemistry and Product Knowledge" pp. 50, 84, 182, 386 and 484 (1996), published by the Chemical Daily.
Encyclopaedia Chimica, vol. 1, p. 751 (1989) published by Kyoritsu Shuppan Co., Ltd.
Encyclopaedia Chimica, vol. 2, p. 216 (1989) published by Kyoritsu Shuppan Co., Ltd.
Encyclopaedia Chimica, vol. 5, p. 950 (1989) published by Kyoritsu Shuppan Co., Ltd.
"Koryo No Jassai Chisiki" (Practical Knowledge of Fragrances), pp. 1-3, Mar. 25, 1975.
Koryo To Choko No Kiso Chishiki (Basic Knowledge of Fragrances and Perfumery), pp. 1-4, Jun. 21, 1995.
Encyclopaedia Chimica, vol. 7, p. 97 (1989) published by Kyoritsu Shuppan Co., Ltd.
Japan Patent Office, Notification of Third Party Submission, Reference No. PO4521209, Dispatch No. 059847, date of dispatch Jul. 16, 2002, date of Notification Jul. 10, 2002 (w/English translation).
Lee, et al., "Perfume composition for deoderizing ammonia odor", Chemical Abstracts Service, 2002:105857, (2000), XP002226338, (abstract). AF.

* cited by examiner

*Primary Examiner*—David J Blanchard
*Assistant Examiner*—Rachael E Welter
(74) *Attorney, Agent, or Firm*—Oblon, Spivak, McClelland, Maier & Neustadt, L.L.P.

(57) ABSTRACT

A hair cosmetic formulation, comprises (A) a fragrance ingredient comprising cis-3-hexenol; and (B) monoethanolamine.

9 Claims, No Drawings

HAIR COSMETIC COMPOSITIONS

CROSS-REFERENCE TO RELATED APPLICATIONS

This application is a continuation-in-part of copending application Ser. No. 09/956,888 filed Sep. 21, 2001.

BACKGROUND OF THE INVENTION

1. Field of the Invention

The present invention relates to hair cosmetic compositions that contain cis-3-hexenol and monoethanolamine in which the cis-3-hexenol not only masks the unpleasant odor of monoethanolamine, but also the mixture of cis-3-hexanol and monoethanolamine imparts a desirable fragrance to the composition.

2. Description of the Background

In hair dye or coloring formulations (hereinafter collectively called "hair coloring formulations"), alkaline agents such as ammonia and monoethanolamine are frequently incorporated therein. The ammonia and amine smells, which these compositions inherently have, have remained unsolved as a serious problem for both those applying the hair coloring formulations and those treated with the formulations. In shampoos, conditioners and other hair care products containing ammonia or monoethanolamine, there also exists the same problem of smells as mentioned above. Thus, there has been a long-standing desire for the development of a method for masking ammonia and amine odors inherent to these formulations. In many hair cosmetic compositions with such hair coloring formulations incorporated therein, on the other hand, a penetration promoter of the aromatic alcohol type is added to promote the penetration of ingredients which act on hair. However, this penetration promoter also imparts a solvent smell to the compositions. These factors have led to a significant need for the development of a method by which the odor of such compositions can be masked.

SUMMARY OF THE INVENTION

Accordingly, one object of the present invention is to provide cosmetic compositions that contain cis-3-hexenol and monoethanolamine, thereby masking the unpleasant odor of monoethanolamine by the cis-3-hexenol, but also provide compositions in which the mixture of cis-3-hexenol and monoethanolamine results in compositions having their own desirable fragrance.

Briefly, this object and other objects of the present invention as hereinafter will become more readily apparent can be attained by a cosmetic formulation, which comprises: (A) a fragrance ingredient comprising cis-3-hexenol, and (B) monoethanolamine.

DETAILED DESCRIPTION OF THE PREFERRED EMBODIMENTS

With a view to ascertaining how to mask the unpleasant smells of hair cosmetic compositions containing monoethanolamine, an investigation has been conducted into the effectiveness of a variety of fragrant materials in masking undesirable odors. As a result, it has been found that addition of cis-3-hexenol, which is called "leaf alcohol" and which has not been considered to be readily useful in formulations as a fragrance because of its grassy smell hair, in an amount greater than its usual amount results in a cosmetic composition which has a very desirable fragrance.

The hair cosmetic composition of the present invention has a desirable fragrance in which the odor of monoethanolamine is effectively masked. The composition also has good stability.

The odor of monoethanolamine can be effectively masked in any cosmetic formulation, particularly for the hair, by cis-3-hexenol. The result of the combination of the two ingredients is distinct without a hint of the odor of either ingredient.

The fragrance ingredient (A) of the present invention contains cis-3-hexenol. As mentioned above, cis 3-hexenol is known as "leaf alcohol" and is a fragrance which is useful for imparting a grassy smell to a formulation containing it. It was, however, not known that this compound is able to mask the odor of monoethanolamine which may be in a composition. To achieve the effective masking and fragrance effect of the invention, it is preferred to add cis-3-hexenol to a composition in an amount of 0.1 to 50 wt. % (hereinafter indicated simply by "%"), preferably from 1 to 50 wt %, especially from 1 to 30% in ingredient (A).

The ingredient (A) may preferably contain, in addition to cis-3-hexenol, one or more substances selected from the group consisting of cis-3-hexenol esters such as cis-3-hexenyl acetate, cis-3-hexenyl formate, cis-3-hexenyl propionate and cis-3-hexenyl salicylate, alcohol C-6, trans-2-hexenol, dimethol (2,6-dimethyl-2-heptanol), dihydromyrcenol (2,6-dimethyl-7-octen-2-ol), citronellol (3,7-dimethyl-6-octen-1-ol), geraniol (3,7-dimethyl-cis-2,6-octadien-1-ol), linalool (3,7-dimethyl-1,6-octadien-3-ol), Magnol™, Sandalmysore Core™ [2-methyl-5-(2,2,3-trimethyl-3-cyclopenten-1-yl)-4-penten-2-ol, product of Kao S. A.], eugenol [2-methoxy-4-(1-propenyl)-phenol], p-cresol, Herbac™ (3,3-dimethylcyclohexyl methyl ketone), Koavone™ (acetyl diisoamylene), γ-methyl ionone [5-(2,6,6-trimethyl-2-cyclohexen-1-yl)-3-methyl-3-buten-2-one], 1-menthone (o-menthan-3-one), Liffarome™ (cis-3-hexenyl methyl carbonate), Manzanate™ (ethyl 2-methylpentanoate, product of Quest Int'l U.K. Ltd.), Fruitate™ [ethyl tricyclo[5.2.1.0]decan-2-ylcarboxylate], o-t-B.C.H.A.(o-t-butylcyclohexyl acetate), p-cresyl acetate, 1,8-cineole, Anethole™, estragol (methyl chavicol), rose oxide [4-methyl-2-(2-methyl-1-propenyl)-tetrahydropyrate] and limonene [p-mentha-1,4(8)-diene]. The ingredient (A) may further contain a solvent as a diluent. Suitable such solvents include dipropylene glycol, triethyl citrate and ethanol. From the standpoint of the emission of a preferred fragrance, the hair cosmetic composition of the present invention can preferably contain ingredient (A) in an amount ranging from 0.1 to 1.0%, especially from 0.3 to 0.8%, based on the weight of the composition.

Ingredient (B) of the present hair cosmetic composition is monoethanolamine which is commonly used as an alkaline agent in oxidation hair colors and hair bleaches. The hair cosmetic composition preferably contains monoethanolamine in an amount of 0 to 20 wt %, especially from 0.1 to 10 wt %, when the hair cosmetic composition is in a form ready for application onto hair (in other words, in a mixed form).

Illustrative hair cosmetic compositions of the present invention include oxidation hair coloring formulations, hair bleaching formulations, acid-dye-based hair coloring formulations, basic-dye-based hair coloring formulations, shampoos, conditioners and other hair care products, all of whose ammonia odor, amine odor and/or solvent odor is as described above. Of these, oxidation coloring formulations are particularly preferred. In the case of an oxidation coloring, an oxidation dye intermediate, for example, a color-developing substance and a coupling agent are added. Suitable examples of the color-developing substance include p-phenylenediamines, 2,5-diaminopyridines, p-aminophenols, o-aminophenols, o-phenylenediamines, and 4,5-aminopyrazoles. Suitable examples of the coupling agent, on the other hand, include various m-phenylenediamines, m-aminophenols, m-hydroxybenzenes, hydroxyindoles, naphthols, and phenols. In addition, a direct dye or the like can also be incorporated in the composition.

When an oxidation dye intermediate is incorporated in a hair cosmetic composition of the present invention, oxidative coupling is induced with oxygen in the air, an enzyme or the like to color the hair or the like. To induce this oxidative coupling, addition of a chemical oxidizing agent is more preferred. Illustrative of the chemical oxidizing agents include hydrogen peroxide, hydrogen peroxide solution, e.g., 35%, urea peroxide, alkali metal bromates, and alkali metal peracid salts, such as perbromates, persulfates or perborates, with hydrogen peroxide being particularly preferred.

In the hair cosmetic composition of the present invention, viscosity/gel strength modifiers, oils and fats, waxes, hydrocarbons, polyhydric alcohols, amides, silicone derivatives, cationic surfactants, anionic surfactants, amphoteric surfactants, nonionic surfactants, nonionic high-molecular substances, cationic high-molecular substances, anionic high-molecular substances, amphoteric high-molecular substances, protein derivatives and amino acids, preservatives, chelating agents, stabilizers, oxidation inhibitors, plant extracts, crude drug extracts, vitamins, color additives, fragrances, pigments, ultraviolet absorbers and the like can be incorporated therein as additives.

Body cleansing formulations and the like, may also contain the combination of cis-3-hexenol and monoethanolamine of the invention.

The pH of the hair cosmetic composition of the present invention preferably ranges from 8 to 12, notably from 9 to 11 when it is an oxidation hair coloring formulation.

EXAMPLES

Example 1

As fragrances in the following hair color cream formula, liquid hair color formulation and hair shampoo formula, the below-described fragrance formula (A) and fragrance formula (B) was added.

Having now generally described this invention, a further understanding can be obtained by reference to certain specific examples which are provided herein for purposes of illustration only and are not intended to be limiting unless otherwise specified.

|  | (Wt %) |
|---|---|
| 1) Hair color cream formula *1 Pack) | |
| Aqueous ammonia (28%) | 1.0 |
| Ammonium bicarbonate | 1.3 |
| Ferrous sulfate | 20 ppm |
| Tetrasodium ethylenediaminetetraacetate | 0.2 |
| Monoethanolamine | 3.0 |
| Monoethanolamine HCl solution (60%) | 1.2 |
| Potassium carbonate | 2.0 |
| Toluene-2,5-diamine | 1.5 |
| Resorcin | 0.6 |
| m-Aminophenol | 0.3 |
| Oleic acid | 10.0 |
| Diethanol oleic acid amide | 8.0 |
| POE(20) octyldodecyl ether | 10.0 |
| Ethanol | 15.0 |
| Propylene glycol | 10.0 |
| Sodium sulfite | 0.5 |
| Ascorbic acid | 0.5 |
| Fragrance | 0.5 |
| Potassium hydrogencarbonate | q.s. to pH 11.0 |
| Water | Balance |
| 2) Liquid Hair Color Formulation *First part agent | |
| Sodium lauroylglutaminate | 5.0 |
| Sodium lauroylsulfate | 5.0 |

-continued

|  | (Wt %) |
|---|---|
| Sodium alkanesulfonate | 3.0 |
| Polyoxyethylene (3) tridecyl ether | 39.0 |
| 2-Benzyloxyethanol | 25.0 |
| Monoethanolamine | 4.0 |
| Aqueous ammonia (28%) | 3.5 |
| Anhydrous sodium sulfite | 0.4 |
| Toluene-2,5-diamine | 1.0 |
| m-Aminophenol | 1.0 |
| Merquat 550 (product of Goodrich) | 4.5 |
| Fragrance | 0.5 |
| Water | Balance |
| *Second part agent | |
| Sodium polyoxyethylene (2) lauryl ether sulfate | 15.0 |
| Polyoxyethylene (9) lauryl ether | 5.0 |
| 35% Aqueous hydrogen peroxide | 17.0 |
| 75% Aqueous solution of phosphoric acid | 0.3 |
| Water | Balance |

The hair color cream formula, the liquid hair color formulation and the hair shampoo formula were organoleptically ranked in smell in accordance with the following 5-stage ranking system by a panel consisting of 5 experts. The results are shown as averages of scores in Table 1.

5: Preferred fragrance

4: No irritating smell

3: Noticeable ammonia smell/solvent smell

2: Strong irritation of ammonia smell/solvent smell

1: Very strong irritation of ammonia small/solvent smell

Table 1

TABLE 1

|  | Examples<br>Fragrance Formula (A) | Comparative Examples<br>Fragrance Formula (B) |
|---|---|---|
| 1) Hair coloring cream formula | 4.8 | 2.4 |
| 2) Liquid hair color formulation | 4.6 | 2.2 |

From Table 1, it is understood that addition of a fragrance ingredient containing cis-3-hexenol makes it possible to markedly mask the ammonia odor and the odor of monoethanolamine containing compositions and hence provides a preferred fragrance.

| 3) Hair Shampoo Formula | (Wt %) |
|---|---|
| Sodium Lauryl Sulfate (Emal 227-PH11 (W) (act27%), Kao Corp) | 40.75 |
| Lauramidopropyl Betaine (Amphitol 20AB, Kao Corporation) | 13.33 |
| Cocamide MEA (Amisol CME, Amisol Company) | 0.80 |
| Sodium Cocoamphoacetate (Amphitol 20Y-B, Kao Corporation) | 2.00 |
| Dimethicone Copolyol Butyl Ether (Silicone KF6012) | 0.20 |
| Polyquaternum-10 (Caticelo M-80) | 0.40 |
| Ethyl alcohol | 2.50 |
| Etidronic Acid (Dequest 2010CS, Solutia Inc.) | 0.50 |
| Monoethanolamine | 10.00 |
| Fragrance | 0.50 |
| Water | Balance |

| | Results | | | | | | | | | | | |
|---|---|---|---|---|---|---|---|---|---|---|---|---|
| | Cis-3-Hexenol in a Fragrance Agent (wt %) | | | | | | | | | | | |
| | None | 0.1 | 0.5 | 1 | 3 | 5 | 8 | 10 | 20 | 30 | 40 | 50 |
| 1) Liquid Hair Color Formulation | 1 | 3 | 4 | 5 | 5 | 5 | 5 | 5 | 5 | 5 | 5 | 5 |
| 2) Hair Shampoo Formula | 1 | 3 | 3 | 5 | 5 | 5 | 5 | 5 | 5 | 5 | 6 | 6 |

Legend
1) Very strong amine smell
2) Strong amine smell
3) Available amine smell
4) Preferred fragrance
5) Strong smell of cis-3-hexanol The disclosure of Japanese priority Application No. 2000-286644, filed Sep. 21, 2000 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A method, which comprises:
   improving the odor of a monoethanolamine containing hair cosmetic formulation by combining in the formulation (i) an amount of fragrance ingredient (A) ranging from 0.1 to 1.0% by wt. that contains from 1 to 50 wt. % of cis-3-hexenol and (ii) an amount of 0.1 to 10.0% by wt. monoethanolamine, the formulation having a pH ranging from 8 to 12 and the interaction of monoethanolamine and cis-3-hexenol producing a distinct odor that is different from the individual odors of monoethanolamine and cis-3-hexenol.

2. The method according to claim 1, wherein said hair cosmetic formulation is an oxidation hair coloring or hair bleaching formulation.

3. The method according to claim 1, wherein said fragrance ingredient (A) further comprises at least one substance selected from the group consisting of cis-3-hexenol esters, trans-2-hexenol, dimethol, dihydromycrenol, citronellol), geraniol, linalool, 2-methyl-5-(2,2,3-trimethyl-3-cyclopenten-1-yl)-4-penten-2-ol, eugenol, p-cresol, 3,3-dimethylcyclohexyl methyl ketone, acetyl diisoamylene, methyl ionone, 1-menthone, cis-3-hexenyl methyl carbonate, ethyl 2-methylpentanoate, ethyl tricyclo[$5.2.1.0^{2,6}$]decan-2-ylcarboxylate, p-cresyl acetate, 1,8-cineole, p-propenylanisole, estragol, rose oxide and limonene.

4. The method according to claim 1, wherein the content of ingredient (A) ranges from 0.3 to 0.8%, based on the weight of the formulation.

5. The method according to claim 1, wherein, when the formulation is an oxidation coloring composition of an oxidation dye intermediate, the formulation additionally comprises a color-developing substance and a coupling agent.

6. The method according to claim 5, wherein the color-developing substance is a p-phenylenediamine, a 2,5-diaminopyridine, a p-aminophenol, a o-aminophenol, a o-phenylenediamine, or a 4,5-aminopyrazole.

7. The method according to claim 5, wherein the coupling agent is a m-phenylenediamine, a m-aminophenol, a m-hydroxybenzene, a hydroxyindole, a naphthol or a phenol.

8. The method according to claim 1, wherein the formulation comprises at least one additive selected from the group consisting of viscosity/gel strength modifiers, oils and fats, waxes, hydrocarbons, polyhydric alcohols, amides, silicone derivatives, cationic surfactants, anionic surfactants, amphoteric surfactants, nonionic surfactants, nonionic high-molecular substances, cationic high-molecular substances, anionic high-molecular substances, amphoteric high-molecular substances, protein derivatives and amino acids, preservatives, chelating agents, stabilizers, oxidation inhibitors, plant extracts, crude drug extracts, vitamins, color additives, pigments and ultraviolet absorbers.

9. A method of treating the hair, which comprises: applying an oxidation hair coloring or hair bleaching formulation to the hair, wherein the applied formulation comprises (A) from 0.1 to 1.0% by wt. a fragrance ingredient that contains from 1 to 50% by wt. cis-3-hexenol, and (B) from 0.1 to 10.0% by wt. monoethanolamine, the formulation having a pH ranging from 8 to 12 and the interaction of monoethanolamine and cis-3-hexenol producing a distinct odor that is different from the individual odors of monoethanolamine and cis-3-hexenol.

* * * * *